(12) United States Patent
Anakwenze (10) Patent No.: US 12,011,154 B1
(45) Date of Patent: Jun. 18, 2024

(54) SURGICAL BONE STABLE DEVICE AND METHOD OF USE

(71) Applicant: Oke A. Anakwenze, San Diego, CA (US)

(72) Inventor: Oke A. Anakwenze, San Diego, CA (US)

( * ) Notice: Subject to any disclaimer, the term of this patent is extended or adjusted under 35 U.S.C. 154(b) by 506 days.

(21) Appl. No.: 17/332,612

(22) Filed: May 27, 2021

Related U.S. Application Data (63) Continuation-in-part of application No. 15/973,303, filed on May 7, 2018, now Pat. No. 11,045,190.

(60) Provisional application No. 62/602,844, filed on May 8, 2017.

(51) Int. Cl.
| | | |
|---|---|---|
| *A61B 17/072* | (2006.01) | |
| *A61B 17/04* | (2006.01) | |
| *A61B 17/064* | (2006.01) | |
| *A61B 17/068* | (2006.01) | |
| *A61F 2/08* | (2006.01) | |
| *A61B 17/00* | (2006.01) | |

(52) U.S. Cl.
CPC ...... *A61B 17/0401* (2013.01); *A61B 17/0469* (2013.01); *A61B 17/0487* (2013.01); *A61B 17/0642* (2013.01); *A61B 17/068* (2013.01); *A61B 17/072* (2013.01); *A61F 2/0811* (2013.01); *A61B 2017/00871* (2013.01); *A61B 17/064* (2013.01); *A61B 2017/07214* (2013.01); *A61F 2/08* (2013.01); *A61F 2002/0864* (2013.01); *A61F 2220/0016* (2013.01)

(58) Field of Classification Search
CPC . A61B 17/04; A61B 17/0401; A61B 17/0487; A61B 17/0462; A61B 17/0488; A61B 17/064; A61B 17/0642; A61B 17/068; A61B 17/0682; A61B 17/072; A61B 17/07207; A61B 2017/0462; A61B 2017/07214; A61B 2017/00477; A61F 2/08; A61F 2/0811; A61F 2220/0016; A61F 2002/0864
USPC .......... 227/19, 175.1, 176.1; 606/1, 75, 139, 606/151, 219
See application file for complete search history.

(56) References Cited

U.S. PATENT DOCUMENTS

| | | | | |
|---|---|---|---|---|
| 4,586,502 A | * | 5/1986 | Bedi | A61B 17/068 606/151 |
| 5,328,077 A | * | 7/1994 | Lou | A61B 17/0642 227/19 |
| 5,354,292 A | * | 10/1994 | Braeuer | A61F 2/0063 606/1 |
| 5,718,706 A | * | 2/1998 | Roger | A61F 2/0811 606/86 R |
| 5,941,439 A | * | 8/1999 | Kammerer | A61B 17/068 227/67 |
| 6,059,787 A | * | 5/2000 | Allen | A61B 17/0642 606/75 |
| 6,193,733 B1 | * | 2/2001 | Adams | A61B 17/1285 606/151 |

(Continued)

*Primary Examiner* — Scott A Smith
(74) *Attorney, Agent, or Firm* — Richard Eldredge; Eldredge Law Firm (57) ABSTRACT

A bone staple device includes a base; and two legs extending parallel from the base, the two legs each having a tapered end opposite the base; and a cutout region extending through a thickness of the base, the cutout region forming a petal protruding away from the leg; the bone staple device serving as a suture anchor to affix directly to soft tissue.

1 Claim, 6 Drawing Sheets

(56) References Cited

U.S. PATENT DOCUMENTS

| | | | | |
|---|---|---|---|---|
| 6,554,852 B1* | 4/2003 | Oberlander | ........ | A61B 17/0401 |
| | | | | 606/232 |
| 7,749,250 B2* | 7/2010 | Stone | ................ | A61B 17/0482 |
| | | | | 606/232 |
| 8,235,995 B2* | 8/2012 | Focht | ................... | A61B 17/068 |
| | | | | 606/75 |
| 8,579,909 B2* | 11/2013 | Burkus | ................. | A61B 90/94 |
| | | | | 606/86 A |
| 8,668,718 B2* | 3/2014 | Euteneuer | ............ | A61B 17/068 |
| | | | | 606/219 |
| 8,679,123 B2* | 3/2014 | Kinmon | ............. | A61B 17/0642 |
| | | | | 606/75 |
| 9,033,201 B2* | 5/2015 | Euteneuer | .......... | A61B 17/0642 |
| | | | | 606/139 |
| 9,107,661 B2* | 8/2015 | Euteneuer | .............. | A61B 17/56 |
| 9,271,726 B2* | 3/2016 | Euteneuer | .............. | A61B 17/17 |
| 9,370,356 B2* | 6/2016 | Euteneuer | .............. | A61F 2/0811 |
| 9,585,656 B2* | 3/2017 | Taber | ................ | A61B 17/0682 |
| 10,123,796 B2* | 11/2018 | Westling | ............ | A61B 17/0642 |
| 11,045,190 B1* | 6/2021 | Anakwenze | ....... | A61B 17/0401 |
| 11,357,497 B1* | 6/2022 | Anakwenze | .......... | A61F 2/0811 |

* cited by examiner

SURGICAL BONE STABLE DEVICE AND METHOD OF USE

CROSS-REFERENCE TO RELATED APPLICATIONS

The present application is a continuation-in-part of U.S. patent application Ser. No. 15/973,303, filed on May 7, 2018, now U.S. Pat. No. 11,045,190, which claims the benefit of and priority to U.S. Provisional Patent Application No. 62/602,844, filed May 8, 2017, each of which is incorporated herein by reference in its entirety.

BACKGROUND

1. Field of the Invention

The present invention relates generally to surgical bone staple devices and methods of use. More specifically, the invention relates to staple anchors that directly affix soft tissues (e.g. tendons, ligaments, etc.) to bones. In addition, the staple anchors may incorporate suture or features that pass suture to augment the affixation of soft tissues to bone. The staple anchors can be used in either open or arthroscopic procedures. The staple anchors are available in different sizes, which allow the attachment of soft tissues to bones of different sizes and for different applications.

2. Description of Related Art

One need in orthopedic surgery is the secure attachment of soft tissues to bones. While bone anchors are well known to secure suture to bones where the suture can be passed through soft tissue such that when suture knots are tightened the soft tissue in positioned into engagement against the bone surface. Providing a bone staple that directly engages the soft tissue to compress into engagement against bone while the staple securely affixes the soft tissue in place addresses key requirements for soft tissue fixation. Not only would such a bone staple provide secure attachment, tailored compression may be applied between the soft tissue and bone to encourage healing. Stability is also provided between the soft tissue and bone to ensure proper alignment during the healing process.

BRIEF SUMMARY OF THE INVENTION

The field of minimally invasive arthroscopic surgical techniques has rapidly progressed over the last decade and continues to evolve with new techniques and procedures performed through minimally invasive techniques. Rotator cuff surgery represents one of the most common orthopedic surgeries performed. A simple description of this surgery involves identifying the tear, debriding the bone and then securing the torn tendon to the bone providing greater tuberosity. This is almost universally done with the use of suture anchors. The anchor is typically a screw that may be screwed within a pilot hole or impacted into the bone.

Extending out of the anchor are sutures that have to be individually passed through the tissue and then tied down to secure the tendon to bone. This process can be fairly complex depending on training, experience and tear pattern. In addition, it can be a time-consuming process passing sutures individually and tying down. Multiple needle passages can be traumatic to already torn and degenerated tissue. Proper tension/compression is not always achievable with sutures. There is also the issue of "knot security". Knots can become undone or loose.

The objective of the device provides a staple-bracket suture device. Through this device, a skilled surgeon can quickly and efficiently secure the rotator cuff to the bone in a one to two step process. A suture will be passed through the tendon and then through the device for proper positioning and tension. Once appropriate, the tendon is secured to bone through the use of a staple that is impacted through the tendon and into bone. The staple will be small enough to limit excess bone and tissue loss and trauma but large enough to provide enough strength and compression. The staple may include features to increase further pull out strength. It may alternatively incorporate petals, extensions, or other features that increase attachment strength of the staple thus the tendon, ligament, or other soft tissue to bone. It may be made of metal, polymer sheath material, absorbable material with appropriate mechanical properties, or a composite of such materials. It may also be coated with collagen scaffolds, pledgets, or other material to encourage healing and/or reduce stress on the soft tissue. This technology can be applied to all areas of surgery that use suture anchors to secure tissue to bone e.g., labral repairs, ligament repairs and reconstruction. This will greatly decrease surgical time and improve ease of use. It may also lead to increased rates of healing.

The various embodiments of the present invention provide a variety of integrated bone staple devices that affix soft tissue to bone, apply tailored compression between soft tissues and bone, or better enable reinforced attachment of soft tissue to bone such as double row fixation.

The various embodiments incorporate bone staple implants, deployment systems that inserts the implant, and staple anchor features that better affix soft tissue to bone at the insertion sites.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional bone staples. Specifically, the invention of the present application provides a non-invasive and efficient method of joining ruptured or damaged soft tissue to bone to facilitate their healing. This and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The bone staple embodiments included in this application present improvements to increase functionality and clinical utility for embodiments in pending patent application Ser. No. 15/973,303 entitled "Surgical bone staple device and method of use", the contents of these documents are hereby incorporated by reference as if recited in full herein.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIGS. 1-6 depict several embodiments of the invention of the application. It should be understood that the embodiments discussed herein are substantially similar in form and function and share one or more of the features discussed in each embodiment although the features may not be shown specifically with reference to the particular embodiment.

FIGS. 1A to 1D depict various views of a bone staple device 101 exemplified by this disclosure. The bone staple device 101 directly secures soft tissues to bone without using individual suture anchors, allowing a surgeon to institute placement of a fastener to retain the soft tissue on an underlying bone with minimal damage to the soft tissue or the bone. Several embodiments of the bone staple device 101 are contained within this disclosure. The bone staple device includes parallel legs 103, 105 with insertion spikes that include sharp tapered ends 111, 113 to penetrate soft tissue and bone during insertion of the bone staple anchor. The legs include cutout regions 115, 117 to define petals 119, 121 that are pre-shaped outward to engage the inner surface of cortical bone to increase pull-out forces and better ensure tensile strength of the secured soft tissue to bone attachment. The base 123 of the anchor includes holes 125, 127 through which suture may be inserted or affixed to allow additional attachment by passing suture through the soft tissue such that the bone staple anchor can simultaneously affix soft tissue directly to bone while also serving as a suture anchor.

Alternative embodiments incorporate individual sheaths made out of polymer strands braided into a mesh or other geometry that may be secured to the individual petals to enhance engagement within the tapped bone insertion channel such that retraction of the bone staple causes the individual sheath proximal ends to bunch up thereby increasing the attachment between the bone anchor and bone. In this embodiment, not shown, the distal end of the polymer sheath is molded to, heat shrunk around, glued to, or tapered to secure to features of the petals to provide a smooth transition from the sharp ends of the petals and the sheath to facilitate insertion through the channel established by tapping the bone staple through bone tissue. Once inserted, the sheath bunches upon itself thereby expanding in diameter such that it increases the pull force therefore improving attachment of the tendon that is captured between individual petals of the anchor to bone. The proximal ends of the sheaths remain free around the petals but incorporate heat treated or glued ends to provide an edge of the sheath to better engage bone while preventing unraveling of the sheath, especially for sheaths utilizing braids, mesh, or other types of woven strands of polymer line.

Various views of an alternative bone staple anchor 201 are shown in FIGS. 2A to 2D. It should be noted, that all these embodiments may further include sheaths tapered and attached to individual petals to increase the pull force thus the secure attachment of tendon to bone. The embodiment in FIGS. 2A to 2D accounts for the engagement angle during deployment of the bone staple anchor, which is usually not 90 degrees relative to the cortical bone surface. Directing the bone staple anchor at a non-90 degree angle requires matching the angle of the base 203 relative to the legs 205, 207 to ensure the base disperses equal force between the soft tissue to bone engagement and avoids high stress regions which would be created if an edge of the base disproportionately engages and cuts into the soft tissue. Similar to anchor 101, anchor 201 further includes holes 209, 211 as well as petals 213, 215 and any of the other features discussed above.

Figure 1A:
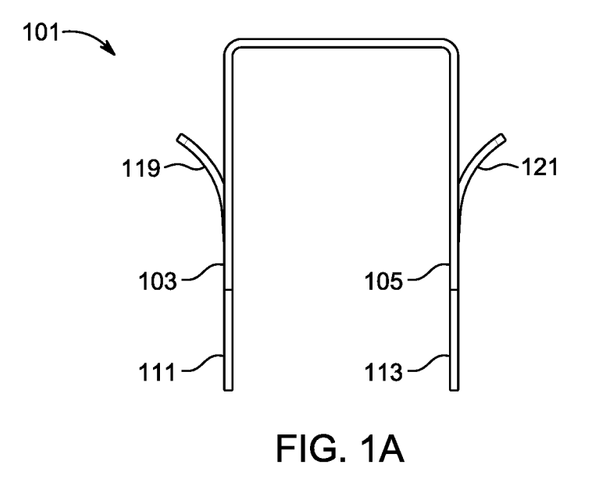
FIGS. 1A to 1D show a bone staple embodiment that uses active fixation to augment the direct attachment of engaged soft tissue to bone.
Figure 1B:
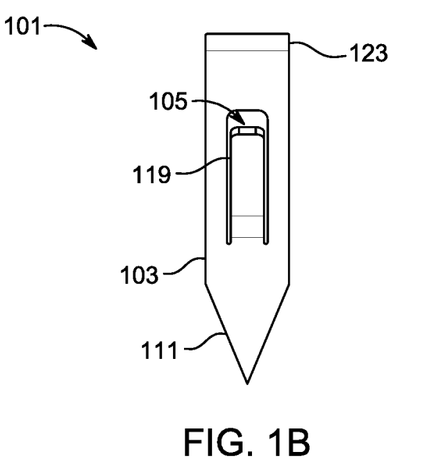
Figure 1C:
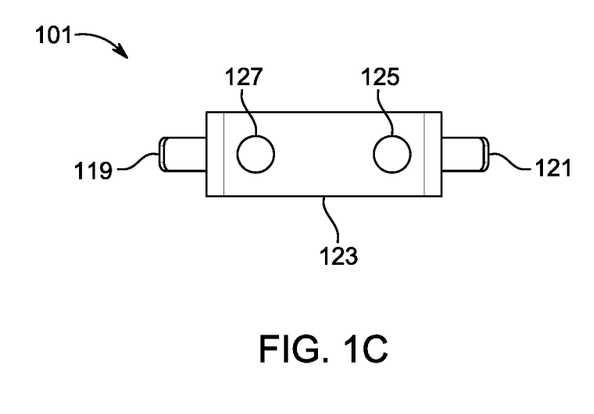
Figure 1D:
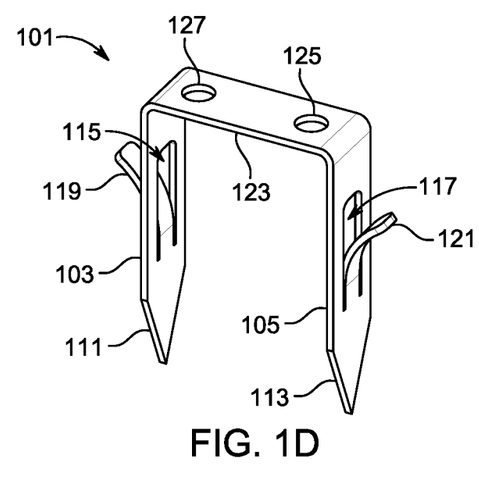
Figure 2A:
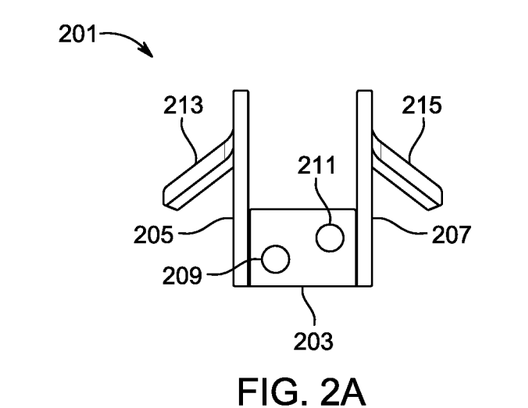
FIGS. 2A to 2D show an alternative bone staple embodiment that uses active fixation to augment the direct attachment of engaged soft tissue to bone.
Figure 2B:
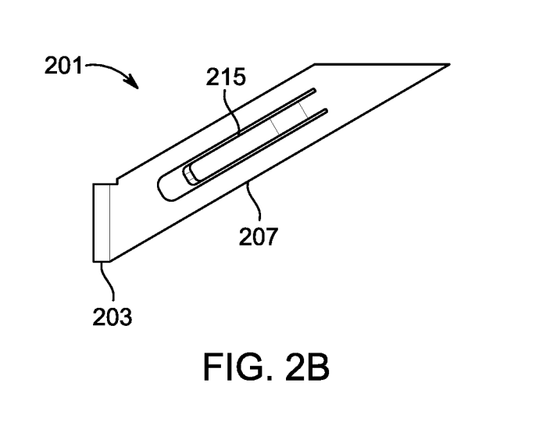
Figure 2C:
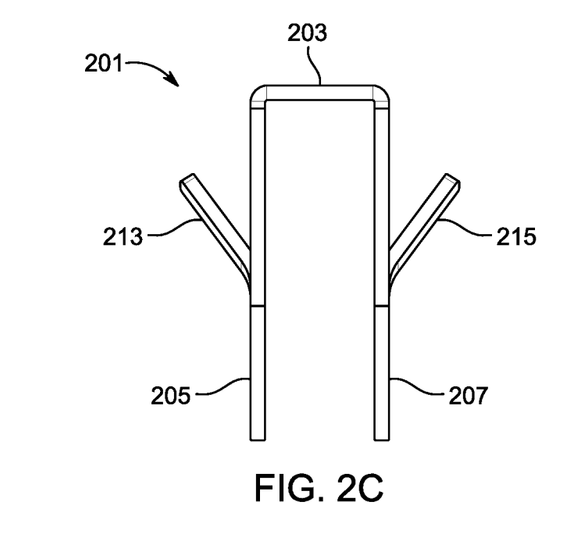
Figure 2D:
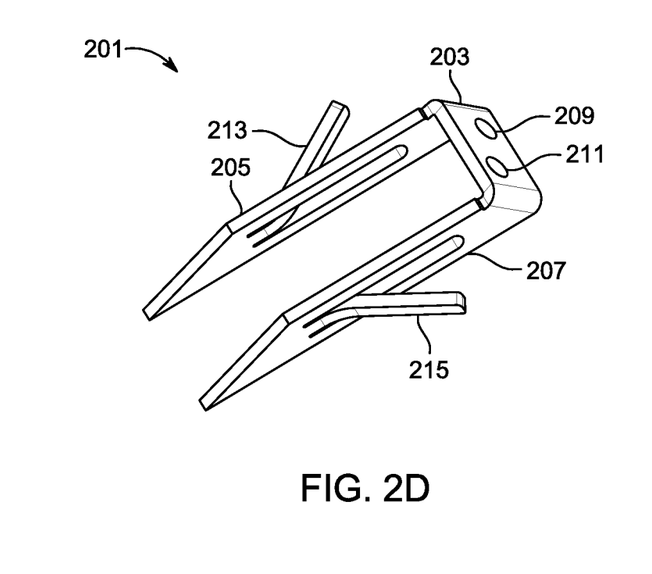
Figure 3:
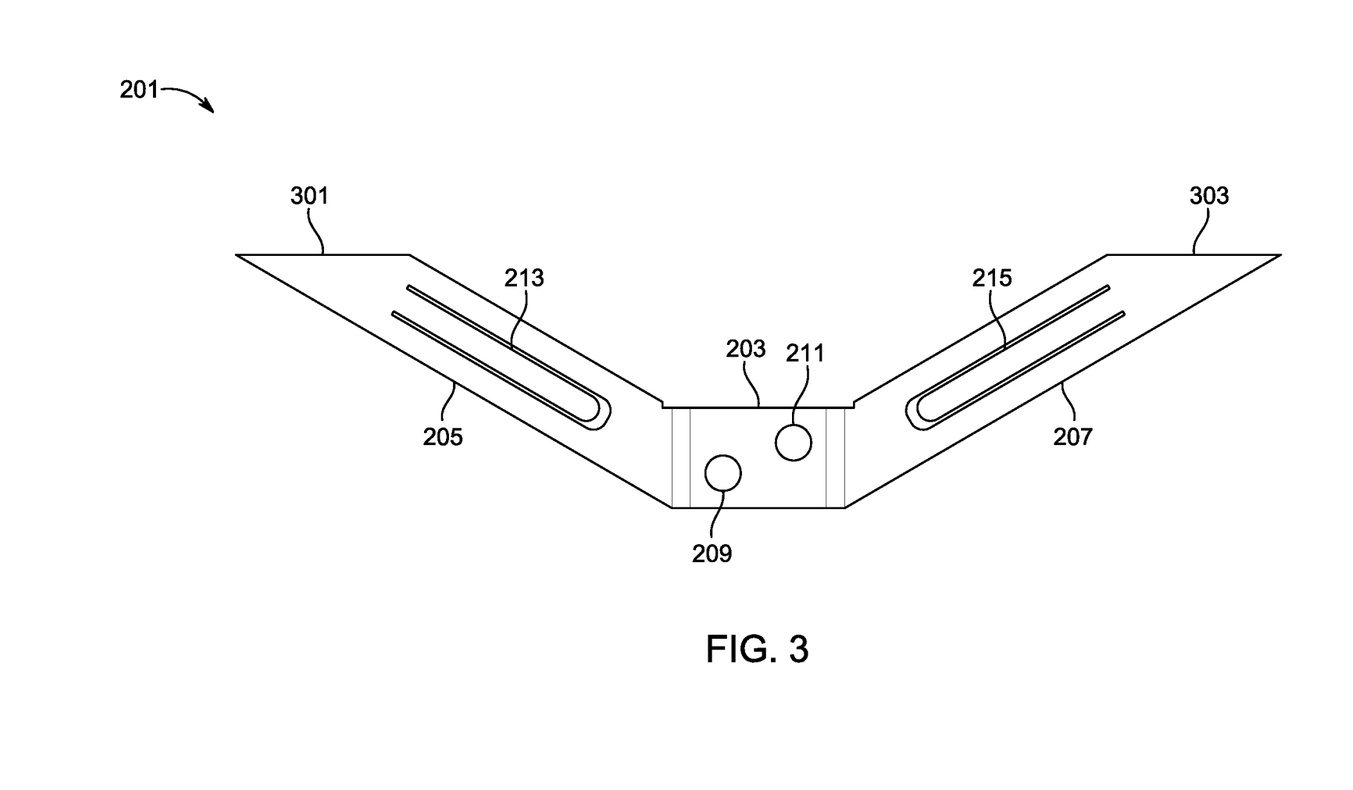
FIG. 3 shows a flattened view of the bone staple embodiment of FIGS. 2A to 2D to facilitate manufacturing processes.

FIG. 3 shows the flattened, manufacturable cutout of the bone staple anchor in FIGS. 2A to 2D prior to forming into the 3-dimensional final product shape. Detailed measurements for various features including the legs 205, 207, insertion spikes 301, 303, petals 213, 215, base 203, and suture holes 209, 211 are shown as illustrative embodiments.

Figure 4A:
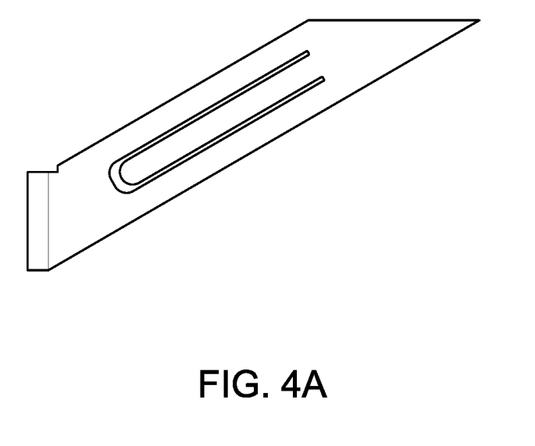
FIGS. 4A to 4C show detailed schematics of one bone staple embodiment shown in FIGS. 2A to 2D and FIG. 3.
Figure 4B:
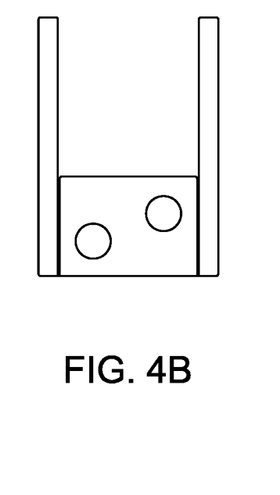
Figure 4C:
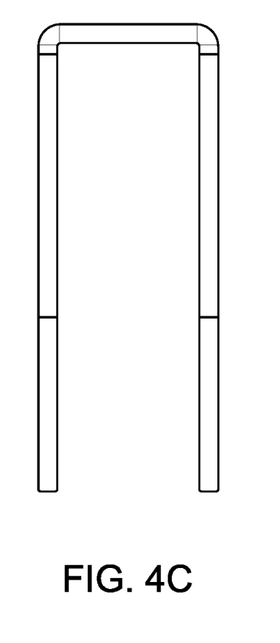

It should be noted that the exact dimensions may be adjusted depending on the application, target soft tissue to bone attachment zone, and patient requirements. The ability to cut the raw material from sheet stock with a desired wall thickness and then preshape into the desired 3-dimensional configuration as shown in FIGS. 4A to 4C, ensures the ability to utilize large volume manufacturing processes such as chemical etching, laser cutting, mechanical cutting, or other process to cut the desired shape. Once the flattened cutout is created, the 3-dimensional preshaped form may be accomplished by standard shape forming processes.

Figure 5:
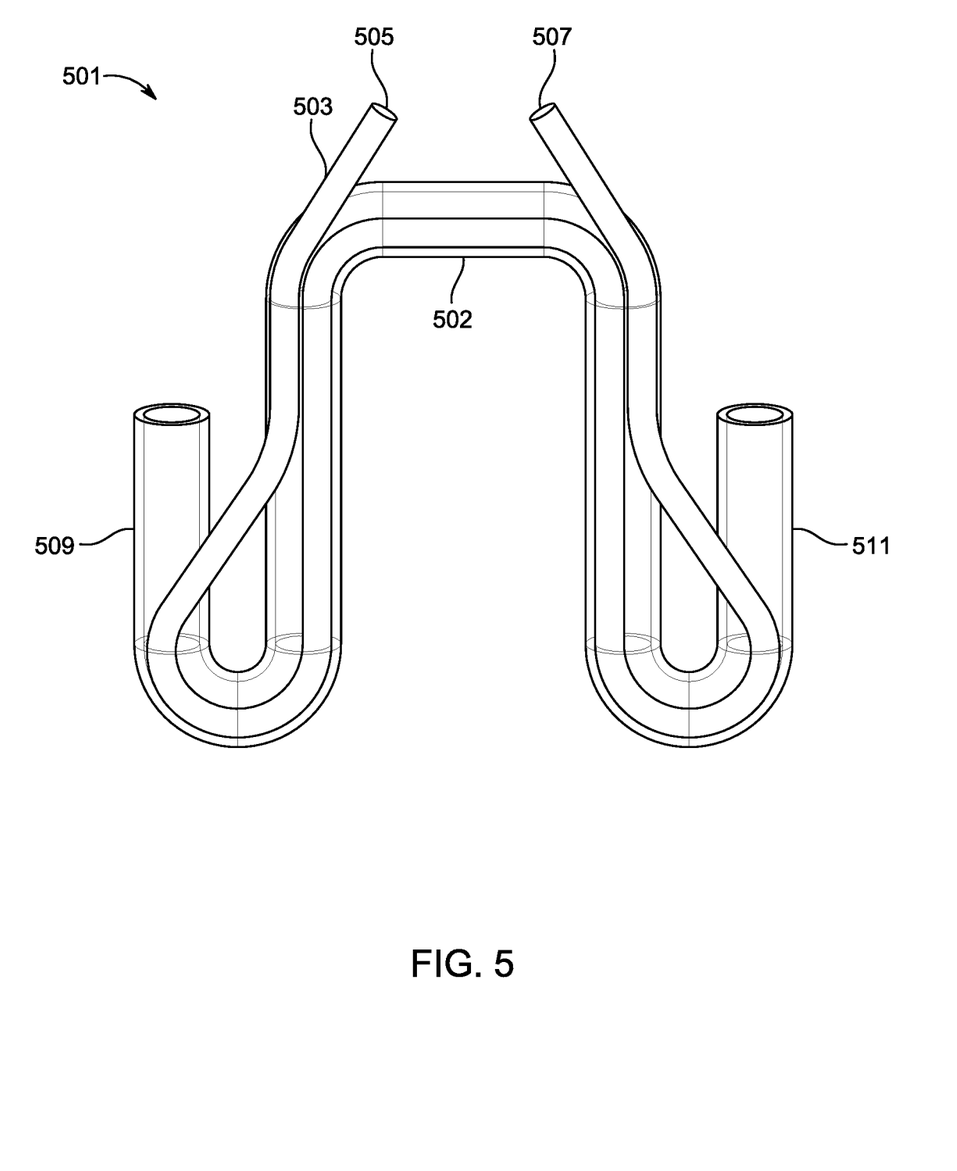
FIG. 5 shows a side view of a bone sheath staple embodiment that integrates a tightening mechanism to lock the sheath in an actuated orientation to secure to bone.

FIG. 5 shows another, completely polymer bone staple anchor 501 embodiment that combines a single suture strand 503 and a single sheath 502 to provide the same attachment of tendon to bone as demonstrated for the bone staples in FIGS. 1 to 4. A single sheath of polymer strands woven into a mesh, braid, or other tubular geometry has ends heat treated, glued, molded, or otherwise stabilized to avoid unraveling of the sheath during or after deployment. A single strand of 2-0 fiber-wire or other strong suture material is fed through the sheath 502 such that the middle portion resides within the sheath while the opposite ends 505, 507 pass through the sides of the sheath at the curved portions 509, 511 of the sheath petals and are fed back through the sheath while exiting just before the base of the bone sheath staple, as shown in FIG. 5. The free ends of the suture may be pre-tied into a knot such that once inserted, retraction of one or more free ends of the suture causes the curved petals to expand in diameter and engage the bone channel through which the petals of the bone sheath staple were tapped. Once full engagement of the bone sheath staple within the bone channel has been obtained, the pre-tied knot maintains the bone sheath staple in the attached orientation and the free ends of the suture may be used to tie to other bone sheath staples to affect a double row anchor or may be passed through other tendons, ligaments, and/or muscle to affix those soft tissues to the bone sheath staple.

It should be noted that the free ends of the sheath may alternatively be secured to the sides of the petals at the locations where the suture strands pass back into the petals past the curved regions and before they exit the base from where they can be tied.

Figure 6A:
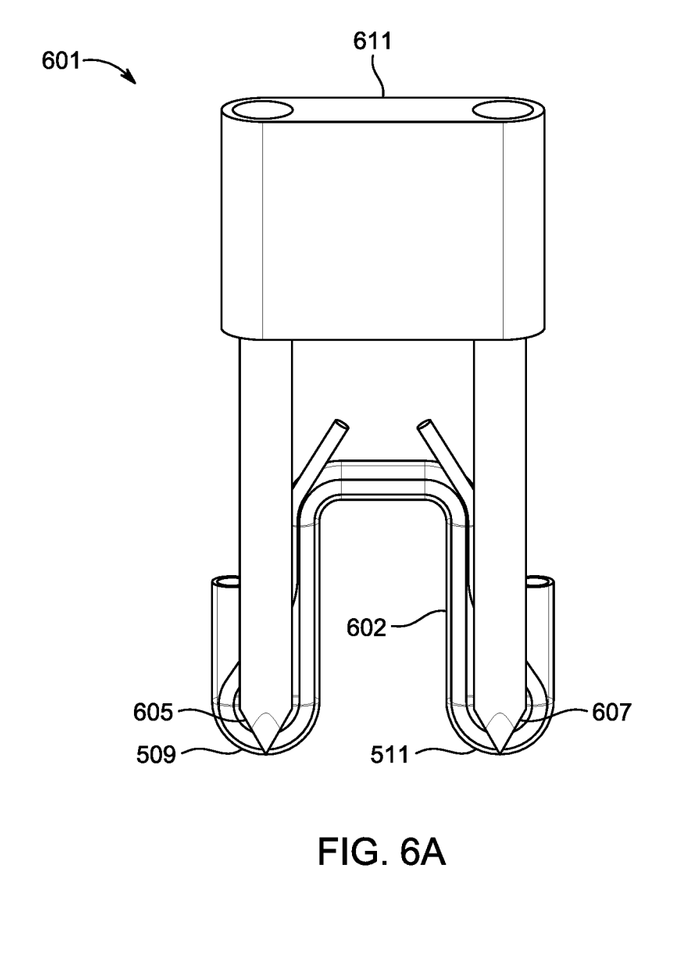
FIGS. 6A to 6C show a deployment system for the bone sheath staple embodiment of FIG. 5.
Figure 6B:
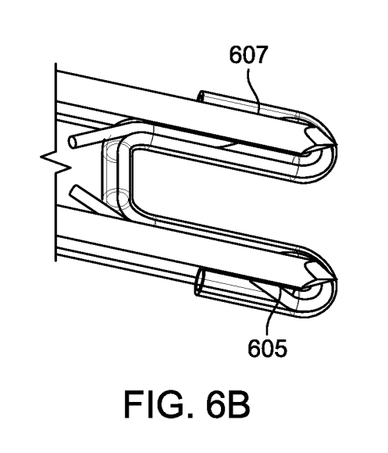
Figure 6C:
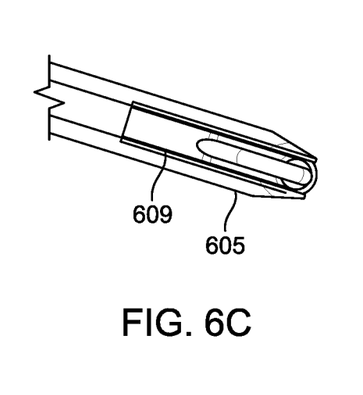

FIG. 6A to 6C shows a deployment system 601 that is used to tap the individual petals of the bone sheath staple 602 into bone to create a channel into which the petals can be activated by tightening of the bone sheath staple suture to attach the staple to the bone. Prior to tapping the bone sheath staple into bone, the deployment system is used to pass the petals of the staple through tendon or other soft tissue such that once the deployment system is used to tap a channel into bone while inserting the petals of the sheath staple into the bone channels and the suture free ends are retracted causing the individual petals to secure the bone sheath staple to the bone, then the tendon or soft tissue engaged against the base of the bone sheath staple is compressed and engaged against the bone. It should be noted that a one way valve involving a stiff polymer with features that allow suture to pass only one way may be used in lieu of pre-tied knot to secure the suture in the retracted orientation thus maintaining the bone sheath staple in the actuated/attached orientation.

The deployment system, as shown in FIG. 6A to 6C, includes two sets of penetrating needles 605, 607 that support the curved ends 509, 511 of the petals during insertion through bone. Each set of penetrating needles includes a distal slot 609 between the sharp ends for the curved ends of the bone sheath staple to reside while inserting through the bone channel. The distal ends of the penetrating needles are sharp so as to create a channel into bone while tapping the bone sheath anchor into channels created by the penetrating needles. Each set of penetrating needles may be fabricated by separate components that are stabilized together or a single needle that includes a central cut-out within which the curved ends of the bone sheath staple reside during deployment.

The deployment system may include a stabilizing bar to support the base of the bone sheath staple, thus the captured tendon or other soft tissue, during deployment. Once the deployment system taps the penetrating needles into bone, creating two parallel channels within which the petal ends of the sheath are simultaneously inserted, the penetrating needles are retracted while the free suture ends are tightened while the stabilizing bar maintains the orientation of the base to ensure the bone sheath staple does not retract while the suture ends are actuated to secure the curved petal ends within the bone channels.

The bone staple and bone sheath staple devices shown are merely representative of several variations and embodiment of the staples. It is not the intent to limit the scope of the staples and instruments used to insert the staples into the tissue, nor to limit the use of the staples to rotator cuff repairs. It is ideal for rotator cuff repairs, but surgeons may choose to use the staples for other soft tissue and other bone attachments. The staples are also not limited to a two prong embodiment and may utilize one staple leg or a plurality of staple legs, with or without sheaths or other features, and in configurations not necessarily linear, including a triangular configuration, a square configuration or a polygon, with more than one bridge between the staple petals or in a geometrical design suitable for the tissue repairs. The staples may be deployed by other apparatuses, although a hard contact implement is not recommended due to the risk of penetration of the soft tissue, deformity or damage to the soft tissue or bone. The staples may be made of metal, thermoplastic, nitinol, suture material, silicone, urethane, PTFE, nylon, other polymer, other biocompatible and bioabsorbable material, or a combination of materials use in implant devices. In addition, coverings may be placed over sections of the bone staple to reduce stresses on soft tissue, further encourage healing, or other purpose that enhances the secure attachment of soft tissue to bone. Although the embodiments of the have been described and shown above, it will be appreciated by those skilled in the art that numerous modifications may be made therein without departing from the scope of the invention as herein described.

While various orthopedic applications benefit from the use of bone staple anchor embodiments of the invention, rotator cuff tendon repair (e.g. partial or complete tears) is one illustrative example that will be described in more detail. The rotator cuff tendon tear is identified and the tendon is debrided. The tuberosity insertion site is likely decorticated. The tendon is approximated to its insertion site. Through percutaneous techniques, arthroscopic cannulas or open approaches the tendon is secured down to the footprint by insertion of the bone staple device into the tendon and then into the bone. Proper petal deployment and resistance to pullout is confirmed by pulling on the device the inserter or sutures that run through it. This device may be used with or without sutures. These sutures may be integrated within the staple as shown for the bone sheath staple embodiments, or preloaded through the suture holes before clip insertion. The sutures may be fed through suture/vent holes of another tendon bone staple anchor embodiment, anchor, or clip. This anchor may then be used to create a double row construct by placing lateral to the initial anchor. It may also be placed medial or lateral to the initial anchor. It should be noted that any number of bone staple anchors may be utilized to ensure proper placement and attachment of soft tissue to bone.

Other applications that benefit from the bone staple anchor include biceps tenodesis where the tendon is secured to the groove, total shoulder arthroplasty where the subscapularis tendon is repaired, attaching grafts when performing procedures such as superior capsular reconstruction, securing grafts to the glenoid, fixing the anterior cruciate ligament, repairing the medial and/or lateral collateral knee ligaments or any application requiring the attachment of soft tissue to bone.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A bone staple system, comprising:
    a staple device sheath having a base and at least two legs extending from the base, the at least two legs having curved portions;
    a suture with two free ends, the suture passing through the sheath such that the two free ends pass through the curved portions;
    wherein the at least two legs pass through soft tissue prior to insertion into bone; and
    wherein tension applied to the two ends of the suture expand the curved ends to secure the staple device sheath to bone and compress the soft tissue against the bone.

* * * * *